United States Patent [19]

Deuar

[11] Patent Number: 5,051,919

[45] Date of Patent: Sep. 24, 1991

[54] TESTING OF POLES

[76] Inventor: Krzysztof J. Deuar, 17 Henderson Road, Burpengary, Queensland, 4505, Australia

[21] Appl. No.: 546,744

[22] Filed: Jul. 2, 1990

Related U.S. Application Data

[63] Continuation-in-part of Ser. No. 396,089, Aug. 21, 1989, abandoned, which is a continuation of Ser. No. 272,477, Nov. 17, 1988, abandoned, which is a continuation of Ser. No. 96,482, Sep. 15, 1987, abandoned.

[30] Foreign Application Priority Data

Apr. 22, 1987 [AU] Australia ............................. 71869/87
Jul. 31, 1989 [AU] Australia ............................. 39091/89

[51] Int. Cl.$^5$ .............................................. G01N 3/20
[52] U.S. Cl. ...................................... 364/508; 73/849; 73/786
[58] Field of Search ............... 364/508, 507, 506, 505, 364/512; 73/849, 816, 807, 788, 786; 254/30, 29 R

[56] References Cited

U.S. PATENT DOCUMENTS

| 2,283,730 | 5/1942 | Gardner. | |
|---|---|---|---|
| 2,854,847 | 10/1958 | Brady | 73/786 |
| 3,733,049 | 5/1973 | van den Hove et al. | 364/508 |
| 4,366,874 | 1/1983 | Pidoux et al. | 364/508 |
| 4,464,937 | 8/1984 | Watts et al. | 73/788 |
| 4,574,356 | 3/1986 | Schattschneider et al. | 364/508 |

Primary Examiner—Parshotam S. Lall
Assistant Examiner—S. A. Melnick
Attorney, Agent, or Firm—Foley & Lardner

[57] ABSTRACT

The residual strength of electricity poles is determined by the deflection of the poles under a pre-determined applied load. The load is applied by an extensible ram which has a foot secured to the base of the pole by a chain and a head plate with teeth which engages the sides of the poles. A preset hydraulic pressure is applied to the ram by a manual pump and the deflection if measured by strain gauges mounted on a support frame. The load deflection data are fed to a programmed computer which calculates the residual strength.

17 Claims, 9 Drawing Sheets

TESTING OF POLES

This application is a continuation-in-part application of Ser. No. 07/396,089, filed Aug. 21, 1989, now abandoned, which is in turn a continuation application of Ser. No. 07/272,477, filed Nov. 17, 1988, now abandoned, which is in turn a continuation application of Ser. No. 07/096,482, filed Sept. 15, 1987, now abandoned.

BACKGROUND OF THE INVENTION

1. Field of the Invention

This invention relates to a method of, and apparatus for, the testing of poles. (Throughout the specification, the term "poles" shall be used to include electricity, telephone and telegraph poles; fence and retaining wall posts and the like.

The term "residual strength" is a measurement of the load which can be applied to a pole before the pole will fall, and is less than the original strength of the pole due to decay, cracking and other factors.

2. Prior Art

Wood rot, bores, termites and other factors operate to reduce the strength, and therefore, the service life of poles. For safety reasons, the strength of the poles must be periodically checked and the future life of the pole established. As wood rot generally occurs below ground level, a simple visual inspection is not sufficient and mechanical strength tests must be carried out.

To date, no simple, efficient and reliable test method has been available so poles are often replaced well before the end of their effective life. This naturally increases the operating expenses of the electricity authority.

SUMMARY OF THE PRESENT INVENTION

It is an object to provide at least one simple method for testing the poles.

It is a preferred object to provide an apparatus suitable for the method.

It is a further preferred object to provide a method where the remaining life of the poles can be calculated.

Other preferred objects will become apparent from the following description.

In one aspect, the present invention resides in a method for the non-destructive testing of the residual strength of a pole including the steps of:

applying a preset load to the pole above ground level;

measuring the displacement of the pole under the load; and from the applied load and the displacement, calculating the residual strength of the pole from predetermined formula(e), or by a programmed calculator or computer.

In a second aspect, the present invention relates to a method for the non-destructive testing of the residual strength of a pole including the steps of:

applying a load to the pole above ground level to cause the pole to undergo a preset displacement;

measuring the load applied to the pole; and from the applied load and the displacement, calculating the residual strength of the pole from predetermined formula(e), or by a programmed calculator or computer.

In a third aspect, the present invention resides in a method for the non-destructive testing of the residual strength of a pole including the steps of:

calculating the minimum required strength of the pole including any required safety factors;

applying a preset load to the pole above ground level equivalent to the calculated minimum strength; and observing if the pole withstands the applied load without failture and so meet the minimum required strength.

In a fourth aspect, the present invention resides in an apparatus for the non-destructive measurement of the residual strength of a pole according to any of the methods hereinbefore described, the apparatus including:

means to apply a load to the pole above ground level;

load cell means to measure the load applied to the pole;

means to measure the displacement of the pole under the applied load; and means to calculate the residual strength of the pole from the applied load and the displacement.

The load may be applied by either pushing or pulling the pole at a height of, eg. 1-2 m above ground level and may be effected by a mechanical jack or turnbuckle, a hydraulic or pneumatic ram, a winch or other suitable mechanical, hydraulic or electrical means.

The applied load is preferably measured by a load cell or other suitable equivalent means.

The displacement of the pole in both deflection and rotation about its vertical arm as well as deformation of the pole is preferably measured and this may be effected by displacement gauges mounted on, or around, a reference frame, strain gauges or the like.

The applied loads, displacements and deformations of the pole may be recorded manually or automatically by the use of any suitable computer system.

Stability of the pole in case of its failure can be provided by a safety frame, safety rope or safety clamps mounted to the boom of the crane, of the pole testing vehicle or other heavy equipment.

The excessive movement of the pole at ground level is limited by a chain, rope, frame, bar or clamps connected to the pole testing equipment or other heavy and stable machinery and objects such as concrete blocks, adjacent trees or the like.

The residual strength and other test parameters may be calculated from predetermined formula(e) or be fed into a programmed calculation or computer.

BRIEF DESCRIPTION OF THE DRAWINGS

To enable the invention to be fully understood, preferred embodiments will now be described with reference to the accompanying drawings, in which.

DETAILED DESCRIPTION OF THE PREFERRED EMBODIMENTS

Figure 1:
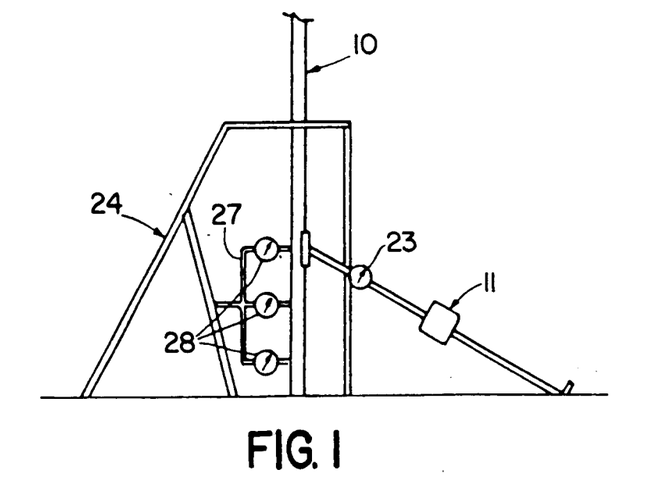
FIG. 1 is a schematic view showing a pole being tested under a preset applied load.
Figure 2:
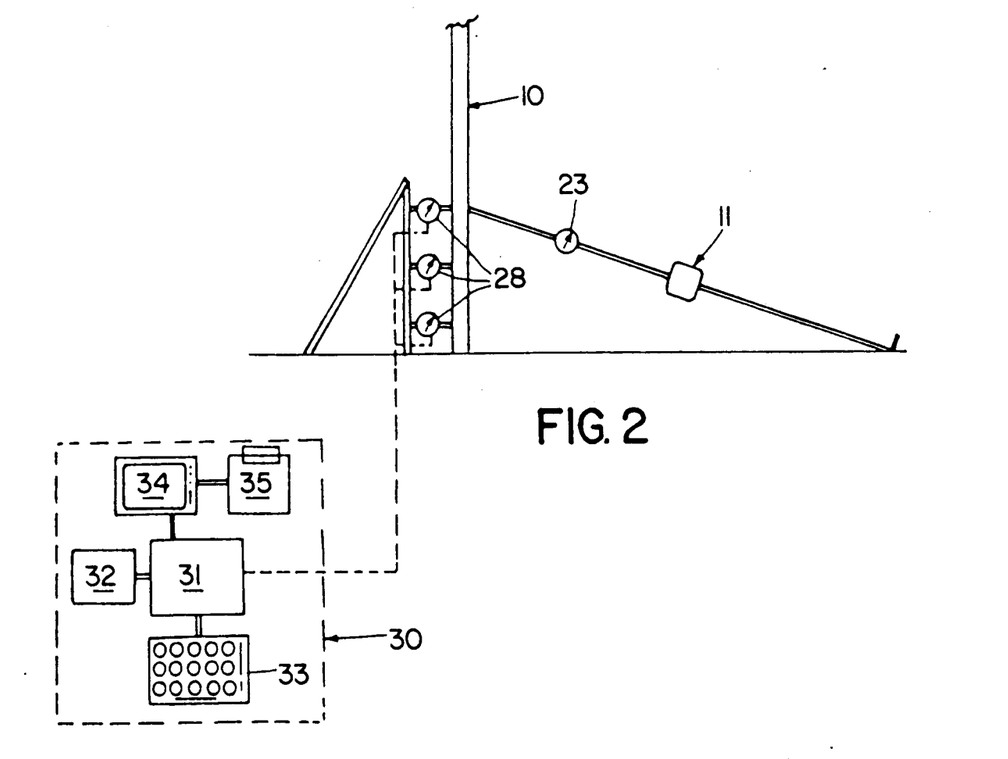
FIG. 2 is a similar view showing a pole being tested under a preset displacement.
Figure 3:
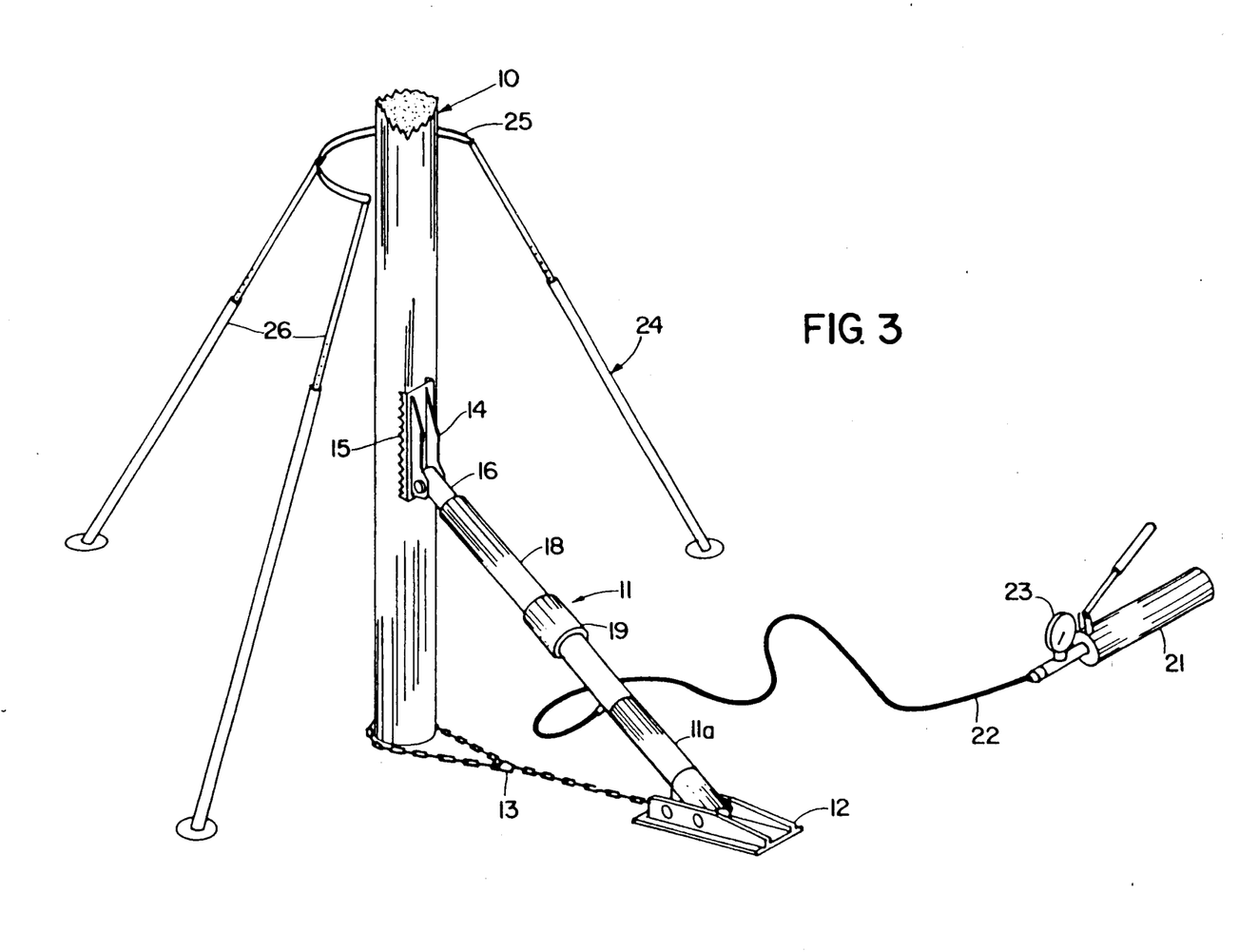
FIG. 3 is a perspective view of the apparatus for applying the load, or displacement, to the pole.

Referring to FIGS. 1 to 3, the residual strength of the pole 10 is measured by the displacement of the pole under a preset applied load of, eg. 100 N.

Figure 4:
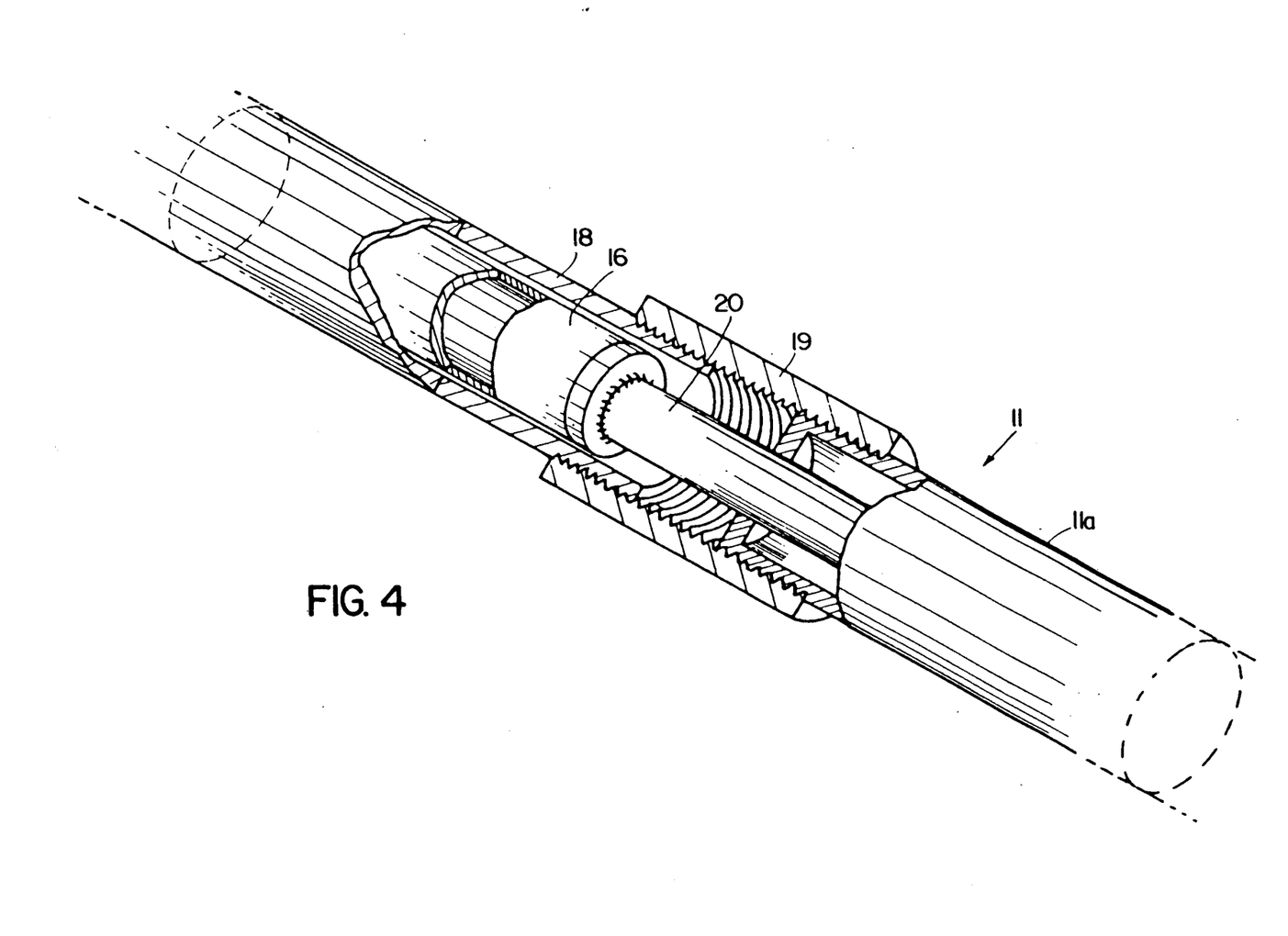
FIG. 4 is a part sectional view of a portion of the ram assembly of FIG. 3.

A pneumatic ram 11 is connected via a bottom tube 11a to a foot 12 anchored to the base of the pole by a chain 13. A head plate 14, with teeth 15, engages the pole 10 and may be releasably secured thereto by nails (not shown). The head plate 14 is mounted on an inner tube 16 telescopically received in an outer tube 17 secured to the ram body 18 by a sleeve 19, the inner end of the inner tube 16 being closed and engaged by the piston rod 20 of the ram 11 (see FIG. 4).

A hand operated pump 21 is connected to the ram 11 by a hose 22 and is fitted with an air pressure valve 23 to enable the applied load to be measured.

A safety frame 24 has a yoke 25 supported on three legs 26 and is positioned to catch and support the pole if the latter should fail under the applied load.

A reference frame 27 may be mounted on the safety frame, or be fixed in the ground, to provide a base reference for a plurality of spaced displacement gauges 28 which are releasably attached to the pole 10. In operation, the ram 11 is extended by operating the pump 21 until a preset load, indicated by the gauge 23, is applied to the pole 11.

The displacement of the pole is read off the displacement gauges 28 (ie. the dial gauges) and the residual strength of the pole is calculated by feeding the applied load and displacement into a programmed hand calculator. (Information such as the height and diameter of the pole; the maximum expected wind forces; the type and number of conductors; and the spacing between the pole and its adjacent poles will have been programmed to display, eg. the maximum applied load and the direction thereof to be applied to the pole.)

If the residual strength of the pole is calculated to be below a set threshold, the pole will be replaced.

Referring now to FIG. 2, the pole 10 is pushed by the ram 11 to a preset displacement, as measured by the displacement gauges 28, and the applied load is read off the gauge 23. The load applied to the pole to generate the present displacement enables the residual strength to be calculated using the calculator or from the tabulated figures.

As shown in FIG. 2, the output of the displacement gauges 28 can be fed directly into the calculator or computer 30 which has a central processor 31 (with a RAM) and a programmed memory 32. The variables such as applied load and pole diameter can be entered via the keyboard 33 and the residual strength may be displayed on a visual display 34 and/or via a printer 35. It will be readily apparent to the skilled addressee that all the data may be captured on site by a suitable recorder and processed later and the processed data may be stored in a history file.

In the method described with respect to FIG. 1, the test load will preferably be greater than the static load on the pole plus the maximum wind load due to any fittings plus an allowance for any additional decay before the next periodic test plus a safety factor. In the method described with reference to FIG. 2, the small test load which generates the preset displacement is extrapolated to calculate the maximum residual strength of the pole.

In a third method, the pole is tested under a Go/No Go situation. The minimum required strength for the pole is calculated based on the maximum wind velocity and any safety factors which must be allowed for. A load equivalent to the minimum required strength is applied to the pole using the ram 11 and the pole is observed. If the pole remains intact, it satisfies the minimum required strength and replacement is not required. This method can be used where the ultimate strength of the pole is not required.

Figure 5:
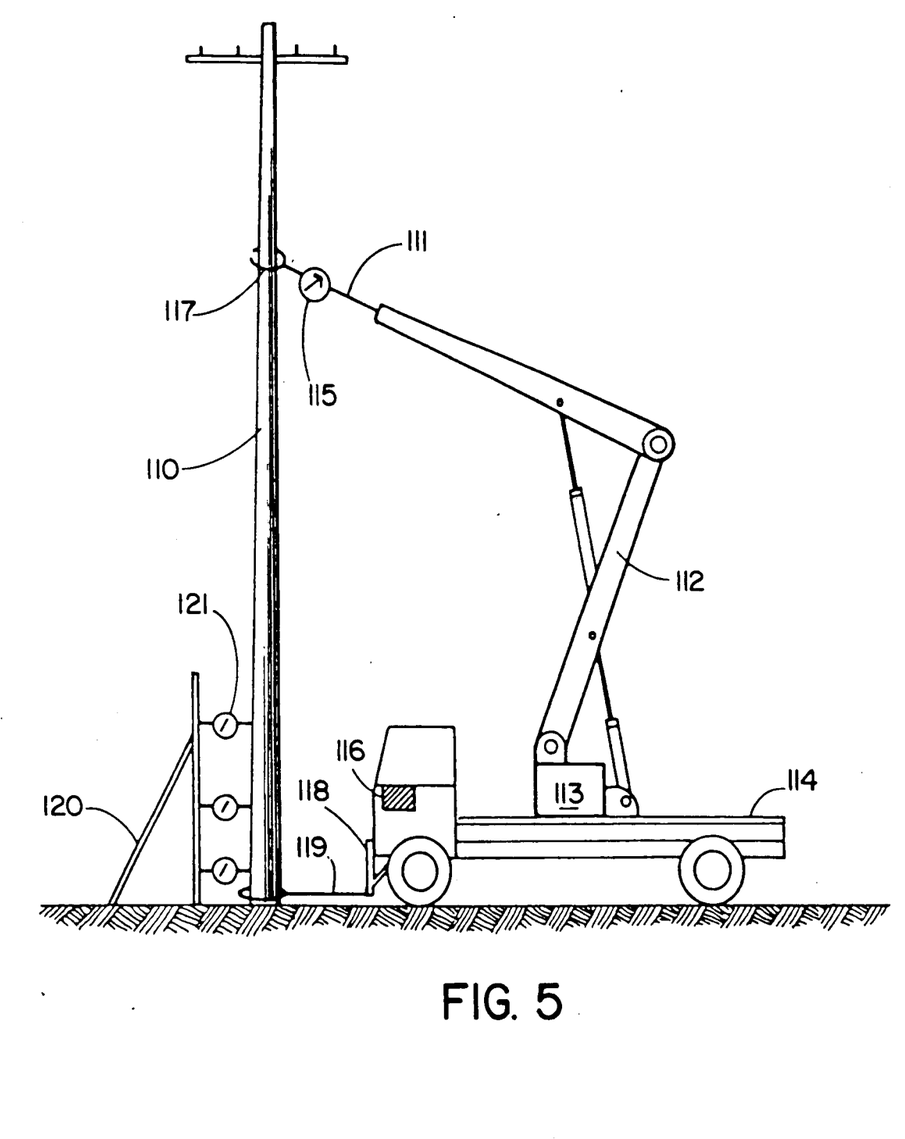
FIG. 5 is a schematic view showing a pole being tested under a preset load.

Referring now to FIG. 5, the residual strength of the pole 110 is measured by the displacement of the pole under a preset applied load of, eg. 100N.

A specially designed boom 111 is a part of a crane 112 powered by a hydraulic unit 113 mounted on a test vehicle 114. A load cell 115 electrically connected to the computer processing unit 116 measure the load applied to the pole 110 or otherwise the load is calculated direcly from the pressure exerted in the hydraulic power unit 113. If necessary, the load is further resolved by a computer 116 into its horizontal and vertical components.

Safety clamps 117 are mounted at the end of the boom 111 to supported the pole both in horizontal and vertical direction should the pole fail under the applied load.

An adjustable length chain 119 is connected to a lowered frame 118 mounted to the test vehicle 114 to prevent the pole 110 from excessive horizontal movement at ground level.

A reference frame 120 provides a base from a plurality of spaced displacement gauges 121 mounted on the reference frame 120 or directly from the hydraulic power unit if the pole deflection is measured at the boom 11 level.

The residual strength of the pole 110 is calculated by feeding the applied load and displacement data into a programmed computer or preferably it can be computed and displayed automatically by the computer processing unit 116. The computer 116 also calculates the minimum required strength for the pole 110 based on the maximum loads applicable to the pole multiplied by a required safety factor allowing for any additional decay before the next periodic test. In this case, additional data are fed through the computer 116 including the size of pole 110, maximum wind forces, the direction, size, number and tension of the wires attached to the pole and other relevant factors. Preferably, the minimum required strength of the pole is determined in the office before the test.

Figure 6:
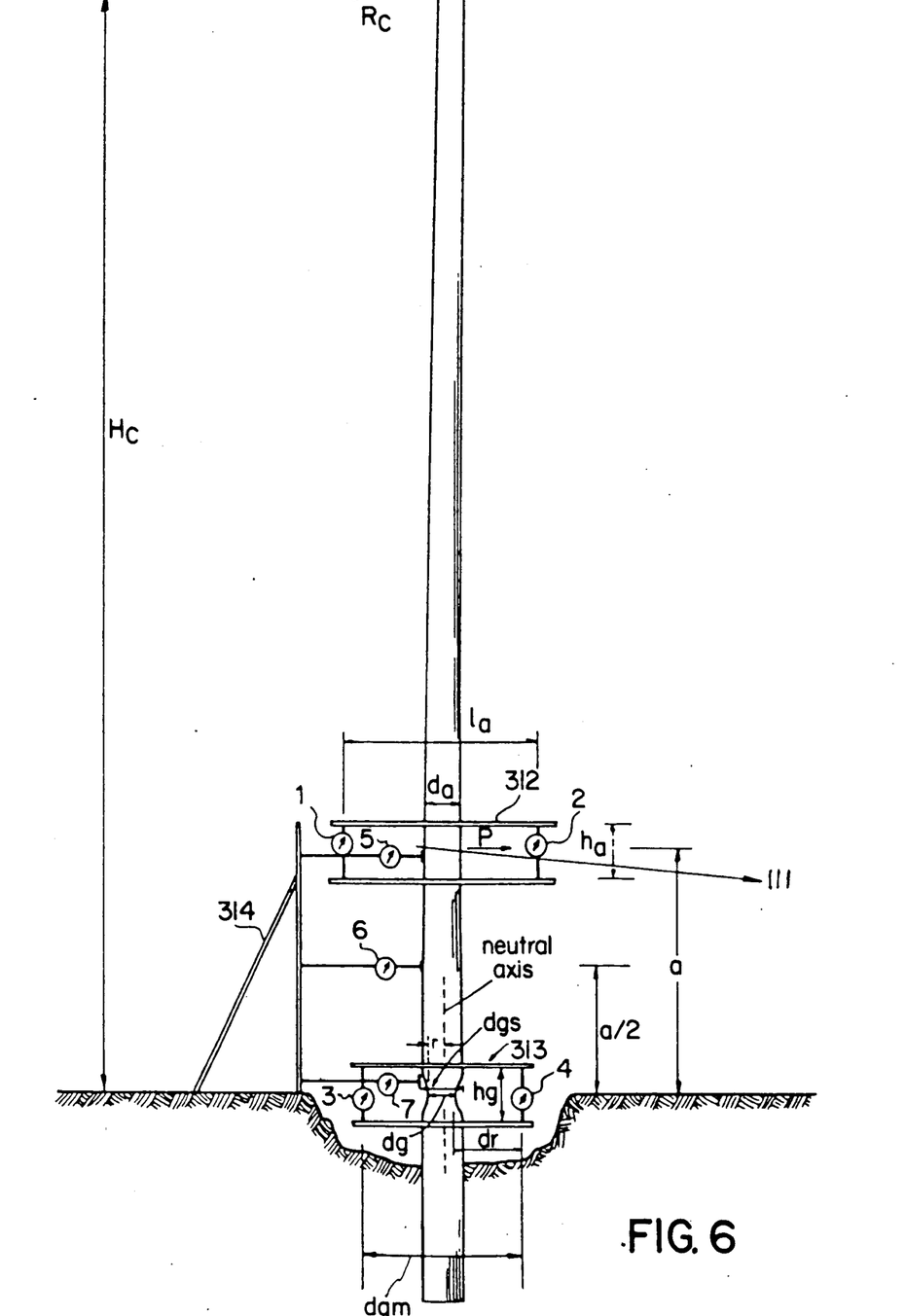
FIG. 6 is a diagram showing an arrangement of dial gauges to predict accurately the residual strength of substantially decayed poles.

Referring now to FIG. 6, the pole is pulled with a preset load P using the winch rope 111 and displacements of the pole are measured using the dial gauges 1 to 7 in order to determine the ultimate bending strength of the pole. The new method of the determination of the residual strength of decayed poles is explained in detail in Appendix 1.

Figure 7:
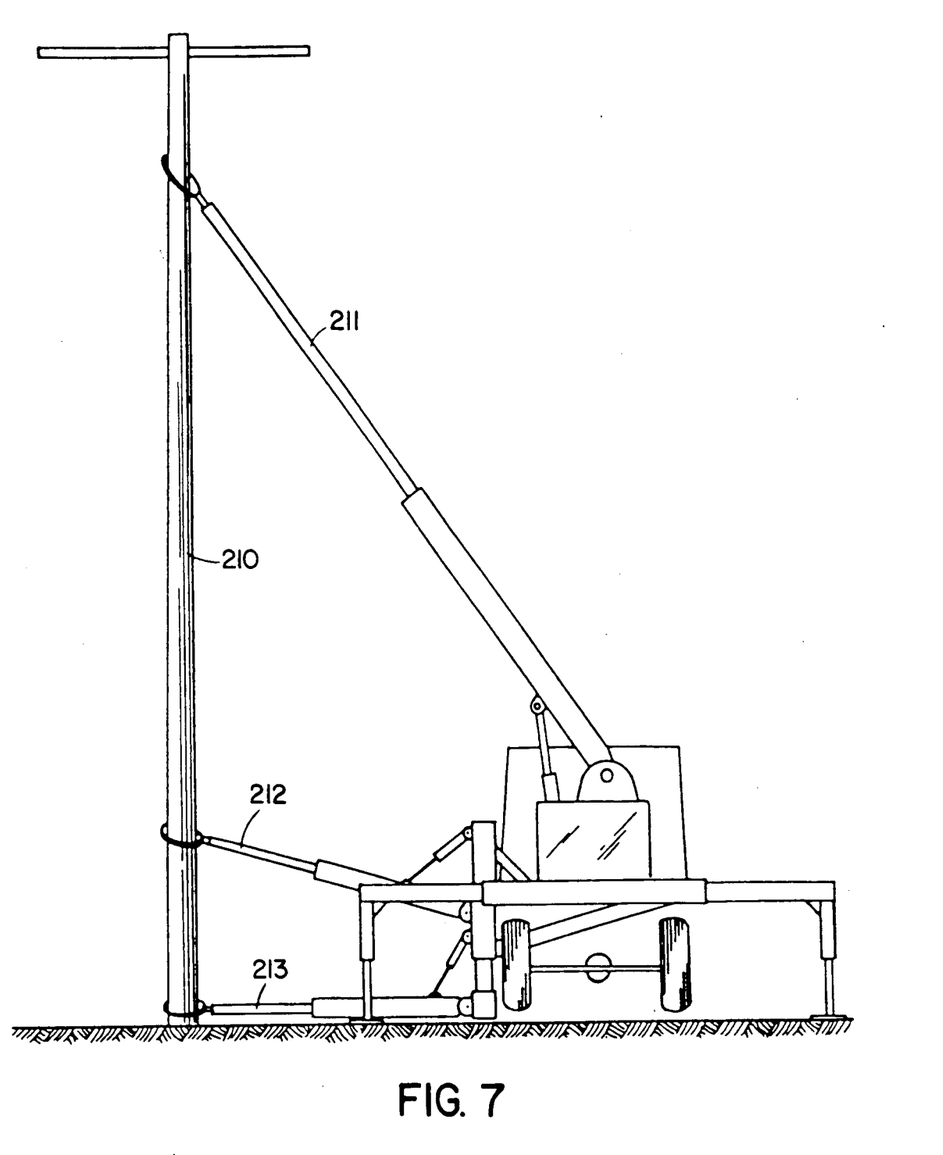
FIG. 7 is a schematic view showing the apparatus for proof loading of standing poles.

With reference to FIG. 7, the pole 210 is tested under a Go/No Go situation. The minimum required strength for the pole is calculated based on the maximum wind velocity and any safety factors which must be allowed for. A load (pushing or pulling) equivalent to the minimum required strength is applied to the pole using hydraulic rams 211, 212 and 213, and hand held or built in computer indicating the applicable oil pressure, and the pole and oil pressure is observed. If the pole fails (oil pressure drops), it must be reinforced or replaced. If the pole remains intact, it satisfies the minimum required strength and replacement is not required. This method can be used where the ultimate strength of the pole is not required.

Figure 8:
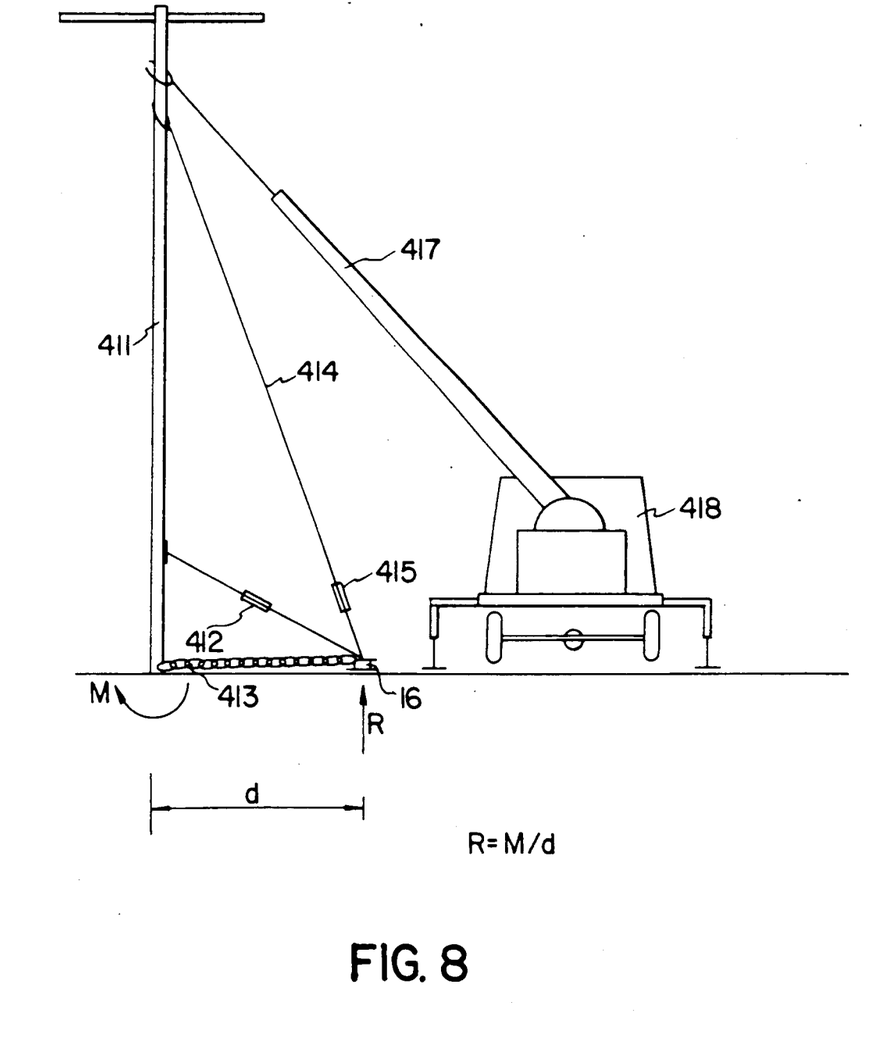
FIG. 8 is a schematic view showing a pole being tested with a portable hydraulic ram.

Referring to FIG. 8, a pole 411 is pushed with a hydraulic ram 412 and simultaneously pulled with a chain 413 and tension rope 414, tensioned by winch 415 until a preset load R is obtained on a load cell 416.

Having the values of the predetermined required strength of pole M and constant distance d between the load cell 416 and pole 411, the load R can be easily calculated from the following formula:

$$R = M/d$$

Stability of the pole in case of its failure is provided by a safety boom 417 of a truck 418. During the test there is no contact between the safety boom 417 and pole 411.

Figure 9:
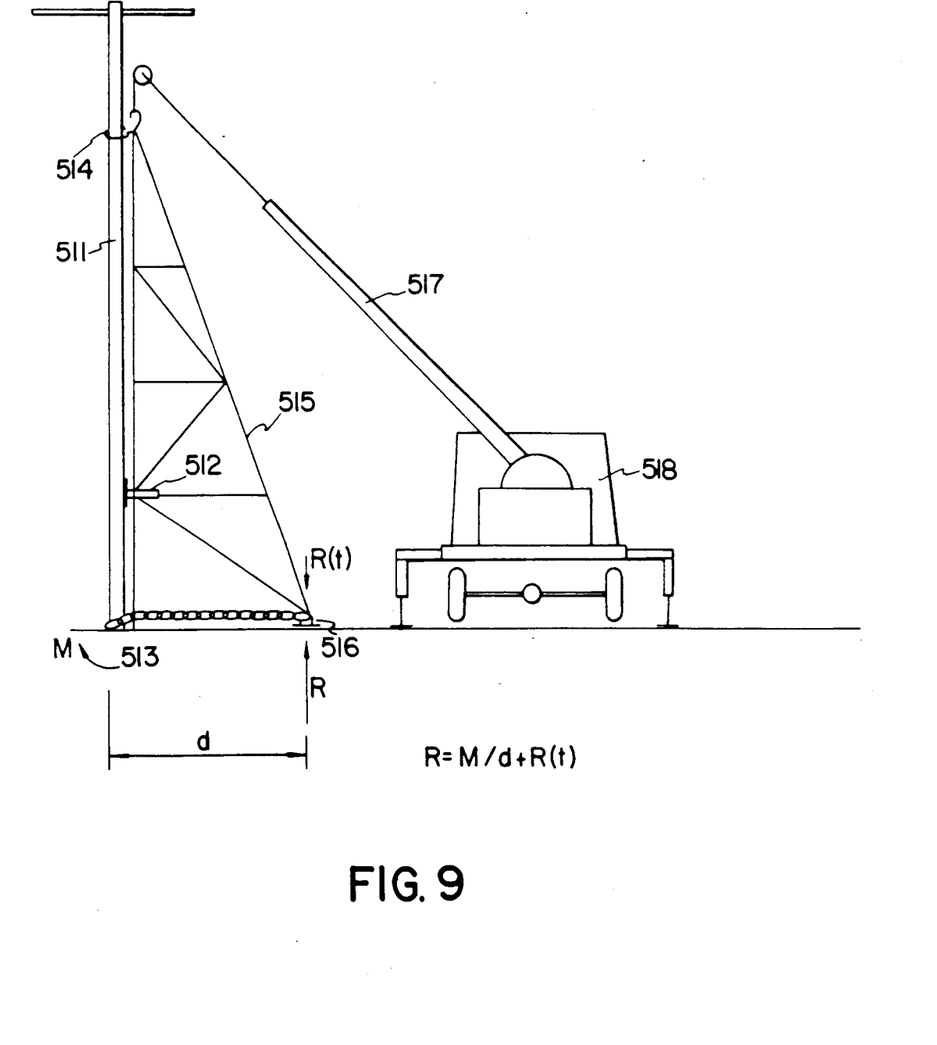
FIG. 9 is a schematic view showing a pole being tested with a specially designed steel truss operated with a crane mounted on a truck.

Referring now to FIG. 9, a pole 511 is pushed with a hydraulic ram 512 mounted on a truss 515 and simultaneously pulled with a chain 513 and a hook 514 attached to the truss 515 until a preset load R is obtained on a load cell 516.

A truss 515 is operated by a crane boom 517 mounted on a truck 518. During the test the truss is resting on the ground, the pole 511 and the load cell 516 and is only loosely hooked to the boom so that there are no forces transmitted between the truss and the boom of the truck.

Having the values of the pre-determined required strength of pole M and constant distance d between the load cell 516 and pole 511, the load R can be easily calculated from the following formula:

$$R = M/d + R(t)$$

where $R(t)$—reaction from the weight of the truss acting on the load cell 16. It can be read from the load cell before the hydraulic ram 12 is activated.

Stability of the pole in case of its failure is provided indirectly (through the truss) by the safety boom 17 of the truck.

Figure 10:
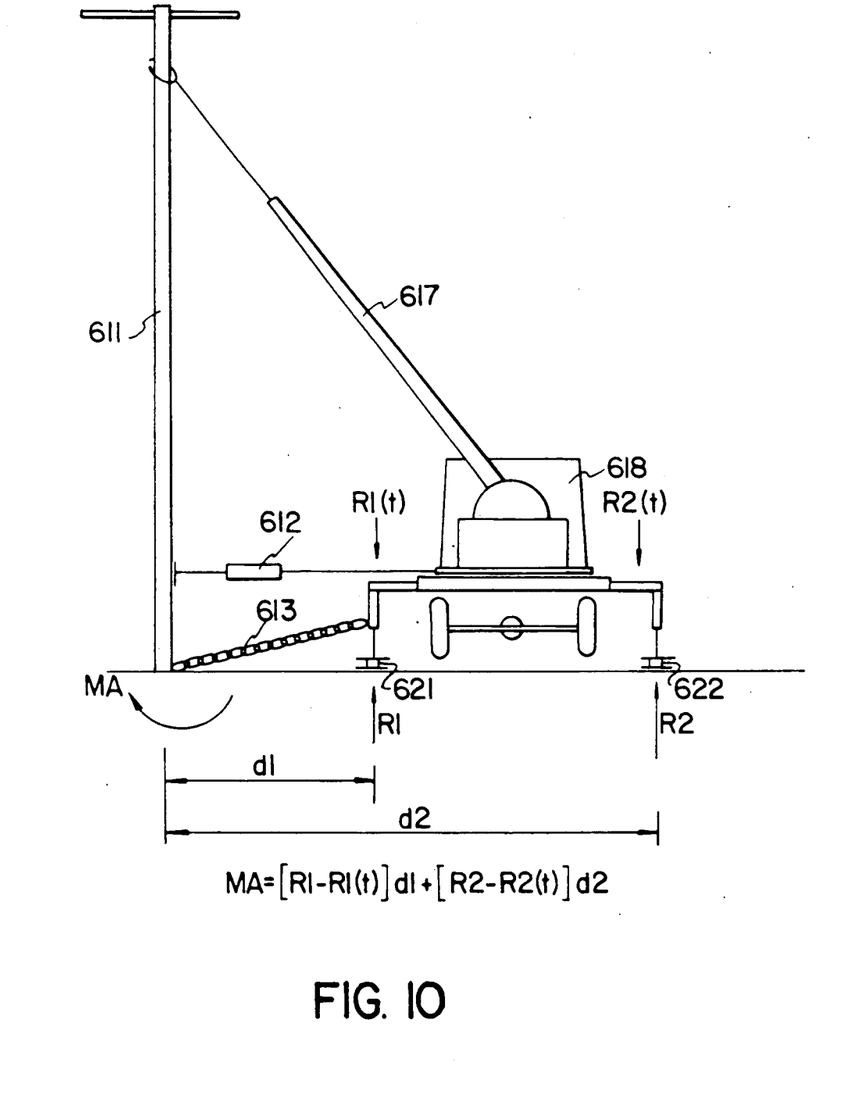
FIG. 10 is a schematic view showing a pole being tested with a hydraulic ram and crane mounted on a truck.

With reference to FIG. 10, a pole 611 is pushed or pulled with a hydraulic ram 612 mounted on a truck 618 and simultaneously pulled or pushed with a passive arm 613 and active boom 617 mounted on the truck until a pre-determined bending moment M on the pole 611 is obtained. During the test the outriggers of the truck 618 rest on load cells 621 and 622.

Having the values of distances d1 and d2 as well as load readings R1 and R2 on load cells 621 and 622 respectively, the actual bending moment MA applied to the pole can be checked easily using the following formula:

$$MA = [R1 - R1(t)]d1 + [R2 - R2(t)]d2$$

where:
MA—actual bending moment applied to the pole at ground level.
R1—load read from load cell 621.
R2—load read from load cell 622.
R1(t)—reaction from the weight of the truck acting on the load cell 621. It can be read from the load cell before the hydraulic ram 612 is activated.
R2(t)—reaction from the weight of the truck acting on the load cell 622. It can be read from the load cell before the hydraulic ram 612 is activated.
d1—distance between the pole 611 and load cell 621.
d2—distance between the pole 611 and load cell 622.

The load generated by the hydraulic ram 612 may need to be increased several times before the actual bending moment MA is equal or greater than the minimum required bending strength of pole M.

Stability of the pole in case of its failure is provided by the load and safety boom 617 of the truck.

In all the embodiments illustrated in FIGS. 8, 9 and 10, the pole is tested under a Go/No Go situation. During the loading both the pole and load cell readings are closely observed. If the pole fails, ie. the pole cracks and load cell reading drops suddenly, the pole is considered unsafe and sooner or later it must be either reinforced or replaced.

The great value of the presented method resides in the fact that despite a complex structural model of the test, including several unknown interactive forces and loads as well as unknown foundation and pole characteristics, only one or few readings are required to check whether a pole has a required strength.

It will be readily apparent to the skilled addressee that the present invention provides simple, efficient and reliable means for determining the residual strength of poles in a non-destructive manner (unless the pole's strength is below a preset safety level).

Various changes and modifications may be made to the embodiments described without departing from the scope of the present invention defined in the appended claims.

APPENDIX 1

FIG. 6 shows a detailed example of the invented method of testing poles and calculating the residual strength of substantially decayed poles at ground line zone.

The horizontal load P is applied by an electric winch 311 fitted on the truck or other suitable means.

Specially designed arms 312 and 313 are used for the attachment of dial gauges 1, 2, 3, and 4 to measure the rotation of the solid wood sections at the level of the application of load P (gauges 1 and 2) and decayed sections of the pole at ground line (gauges 3 and 4).

The tripod 314 serves as the reference base for the measurement of three horizontal pole deflections using dial gauges 5, 6, and 7.

The following formulas are used for the determination of the residual pole strength.

$$M_A = \frac{(Pa - R_c H_c) d_{gm} e_{ult}}{(e_{gL} + e_{gR})r}$$

where:
$M_A$—the residual strength of partially decayed pole at ground line in kNm.
P—the preset horizontal load applied to the pole in kN.
a—the distance from load P to the critical cross-section of the pole at ground line in m.
$R_c$—the resultant reaction of conductors at the top of the pole in kN.

$H_c$—the distance from the conductors to the critical cross-section of the pole at ground line in m.

$d_{gm}$—the horizontal distance between dial gauges 3 and 4 in m.

$e_{ult}$—the ultimate strain of the solid timber fibre.

$e_{gL}$—the strain obtained from dial gauge 1.

$e_{gR}$—the strain obtained from dial gauge 2.

r—the maximum distance from the neutral axis of the decayed cross-section of the pole at ground line to the outer solid timber fibre in m.

Reaction $R_c$ is calculated from the following formula:

$$R_c = \frac{0.098 \, d_a^3 e_a E_a}{H_c - a}$$

where:

$d_a$—the diameter of solid cross-section of the pole at the level of horizontal load P in m.

$e_a$—the solid fibre strain obtained from dial gauges 1 and 2.

$E_a$—the actual modulus of elasticity of solid wood at the level of load P in kN/m².

Strains $e_{gL}$, $e_{gR}$, and $e_a$ are obtained from the following formulas:

$$e_{gL} = \frac{|R3|}{h_g}$$

$$e_{gR} = \frac{|R4|}{h_g}$$

$$e_a = \frac{|R1| + |R2|}{2} \cdot \frac{d_a}{l_a h_a}$$

where:

R1–R4—the readings from dial gauges 1–4 corresponding to applied load P in mm.

$h_g$—the measuring span (vertical) of dial gauges 3 and 4 in mm.

$l_a$—the horizontal distance between dial gauges 1 and 2 in m.

$h_a$—the measuring span (vertical) of dial gauges 1 and 2 in mm.

Distance r can be calculated as:

$$r = \frac{d_g}{2} + \left| \frac{d_g}{2} + d_R - \frac{e_{gR} d_{gm}}{e_g^L + e_{gR}} \right|$$

where:

$d_g$—the diameter of residual solid wood of the critical cross-section of the pole at ground line in m.

$d_R$—the measured distance from the outer fibre of solid wood of the critical cross-section to dial guage 4 in m.

Actual modulus of elasticity $E_a$ and its reciprocal $f_a$ are calculated from the following formulas.

$$E_a = \frac{1}{f_a}$$

and $$f_a = \left[ \frac{a^2 H_c^3 d_a^3 e_a}{2(H_c - a) d_{gs}^4} \cdot \frac{H_c^2 - 0.84 a H_c + 0.133 a^2}{(H_c - 0.34a)^2 (H_c - 0.17a)^2} + V_a 2 V_{a/2} + v_g \right]$$

$$\frac{d_{gs}^2 d_a (d_{gs} + d_a)^2}{(2 d_{gs} + d_a) 3.4 a^3 P}$$

where:

$d_{gs}$—the original diameter of solid wood of the critical cross-section at ground line when the pole was new in m.

$V_a$—the horizontal deflection of the pole at the level of load P in m.

$V_{a/2}$—the horizontal deflection of the pole at the middle of the distance a between the load P and ground line in m.

$V_g$—the horizontal deflection of the pole at ground line in m.

Deflections $V_a$, $V_{a/2}$, and $V_g$ are calculated from the readings of dial gauges 5, 6 and 7.

$$V_a = |R5|/1000$$

$$V_{a/2} = |R6|/1000$$

$$V_g = |R7|/1000$$

Where R5, R6 and R7 are the readings in mm, corresponding to the applied load P, taken from dial gauges 5, 6, and 7.

The above formulas represent a sophisticated structural analysis and therefore a portable hand held computer is required to make the new technique practical for everyday use.

The new method explained by the example is a first known approach to accurately predict the ultimate strength of standing poles which may have a substantial external and internal decay at their critical zone at the ground level.

I claim:

1. A method for the non-destructive testing of the residual strength of a pole comprising the steps of:
    applying a load to the pole by pushing or pulling the pole above ground level to cause the pole to undergo a preset displacement;
    measuring the load applied to the pole;
    measuring the displacement of the pole in both deflection and rotation about its vertical axis using displacement gauges mounted on a reference frame.

2. A method for the non-destructive testing of the residual strength of a pole including the steps of:
    applying a preset load to the pole by pushing or pulling the pole above ground level;
    measuring the displacement of the pole under the load in both deflection and rotation about its vertical axis by displacement gauges mounted on a reference frame; and
    from the applied load and the displacement, calculating the residual strength of the pole from predetermined formula (e) or by a programmed calculator or computer.

3. A method according to claim 2 wherein the formula (e) used to calculate the residual strength of the pole is dependent on factors including the height and diameter of the pole, type and number of conductors supplied by the pole, the spacing between the pole and adjacent poles and the estimated maximum wind forces on the pole.

4. A method according to claim 2, further comprising the steps of:
- calculating the minimum required strength of the pole including any required safety factors;
- applying a preset load to the pole above ground level equivalent to the calculated minimum strength; and
- observing if the pole withstands the applied load without failure and so meets the minimum required strength.

5. An apparatus for the non-destructive testing of the residual strength of a pole comprising:
- means for applying a load to the pole above ground level, comprising at least one of a chain and a cable which is tensioned by a winch;
- means for measuring the load applied to the pole, comprising a load cell or a gauge;
- means for measuring a displacement of the pole under the applied load; and
- computer means for calculating the residual strength of the pole from the applied load and the displacement.

6. An apparatus as claimed in claim 5, wherein the load is applied by pushing or pulling the pole above ground by a pneumatic or hydraulic ram.

7. An apparatus according to claim 6, wherein the pneumatic or hydraulic ram has a cylinder with a foot anchored thereto, the foot being spaced from the pole by the cable or chain; and
- a head plate engaged with the pole, the head plate being fixed to the distal end of an inner tube which is telescopically received in an outer tube mounted on the ram, the inner tube being engaged by the piston rod of the ram.

8. An apparatus according to claim 5, further comprising a vehicle; and
- a pneumatic or hydraulic ram which is incorporated in a boom which is mounted on the vehicle, the boom having a distal end which engages the pole.

9. An apparatus according to claim 5, further comprising a vehicle, wherein the means for measuring the load comprises at least one of displacement gauges and strain gauges in communication with the vehicle and which measure a change in the weight of the vehicle on the gauges.

10. An apparatus according to claim 5, wherein the residual strength is calculated in a programmed calculator or a computer.

11. An apparatus for the non-destructive testing of the residual strength of a pole comprising:
- means for applying a load to the pole above ground level;
- means for measuring the load applied to the pole;
- means for measuring the displacement of the pole under the applied load about its vertical axis in both deflection and rotation, comprising displacement or strain gauges mounted on a reference frame; and
- computer means for calculating the residual strength of the pole from the applied load and the displacement.

12. An apparatus as claimed in claim 11 wherein the load is applied by pushing or pulling the pole above ground level by a mechanical jack or turnbuckle, the means for measuring the load comprising a load cell or gauge.

13. An apparatus as claimed in claim 11 wherein the load is applied by pushing or pulling the pole above ground by a pneumatic or hydraulic ram, the means for measuring the load comprising a load cell or gauge.

14. An apparatus according to claim 13 wherein the pneumatic or hydraulic ram has a cylinder with a foot anchored thereto, the foot being spaced from the pole by a cable or chain; and
- a head plate engaged with the pole, the head plate being fixed to the distal end of an inner tube which is telescopically received in an outer tube mounted on the ram, the inner tube being engaged by the piston rod of the ram.

15. An apparatus according to claim 11 further comprising a vehicle; and
- a pneumatic or hydraulic ram which is incorporated in a boom which is mounted on a vehicle, the boom having a distal end which engages the pole.

16. An apparatus according to claim 11 further comprising a vehicle; and
- wherein the means for measuring the load comprises at least one of displacement gauges or strain gauges in communication with the vehicle and which measure a change in the weight of the vehicle on the gauges.

17. An apparatus according to claim 11, wherein the residual strength is calculated in a programmed calculator or a computer.

* * * * *